US011298186B2

(12) United States Patent
Chou et al.

(10) Patent No.: US 11,298,186 B2
(45) Date of Patent: Apr. 12, 2022

(54) SURGERY ASSISTIVE SYSTEM AND METHOD FOR OBTAINING SURFACE INFORMATION THEREOF

(71) Applicant: POINT ROBOTICS MEDTECH INC., Hsinchu (TW)

(72) Inventors: Hao-Kai Chou, Hsinchu (TW); Chih-Min Yang, Hsinchu (TW); Chia-Ho Yen, Hsinchu (TW); Shou-An Yu, Hsinchu (TW); Wei-Jhen Huang, Hsinchu (TW); Che-Wei Su, Hsinchu (TW); Shyue-Cherng Juang, Hsinchu (TW)

(73) Assignee: Point Robotics Medtech Inc., Hsinchu County (TW)

( * ) Notice: Subject to any disclaimer, the term of this patent is extended or adjusted under 35 U.S.C. 154(b) by 99 days.

(21) Appl. No.: 16/052,652

(22) Filed: Aug. 2, 2018

(65) Prior Publication Data

US 2020/0038108 A1 Feb. 6, 2020

(51) Int. Cl.
*A61B 34/10* (2016.01)
*A61B 17/34* (2006.01)
(Continued)

(52) U.S. Cl.
CPC .......... *A61B 34/10* (2016.02); *A61B 17/1703* (2013.01); *A61B 17/3423* (2013.01);
(Continued)

(58) Field of Classification Search
CPC ..... A61B 34/10; A61B 34/74; A61B 17/1703; A61B 17/3423; A61B 2034/105;
(Continued)

(56) References Cited

U.S. PATENT DOCUMENTS 5,440,392 A * 8/1995 Pettersen ............. G01B 11/002
356/620
5,871,018 A * 2/1999 Delp ....................... G06T 19/20
128/898
(Continued)

FOREIGN PATENT DOCUMENTS

CN 102908143 A 2/2013
CN 102933163 A 2/2013
(Continued)

*Primary Examiner* — Carl H Layno
*Assistant Examiner* — Manolis Pahakis
(74) *Attorney, Agent, or Firm* — Li & Cai Intellectual Property Office

(57) ABSTRACT

A surgery assistive system includes an instrument having a tool and a manipulator connected to the tool, a spatial sensor system for detecting spatial information of the tool, and a computer system for manipulating a kinematic state of the manipulator. A method for obtaining surface information by the surgery assistive system includes the steps of: defining a target region and a plurality of reference points on a virtual anatomical model of a subject; prompting a user to generate sampling information by using the instrument to sample a plurality of sampling points on the subject corresponding to the reference points; and designating the sampling information as surface information of the sampling points. Each piece of the sampling information includes a coordinate of one of the sampling points, an angle of a contact of the tool at the sampling point, and parameters associated with the contact.

11 Claims, 16 Drawing Sheets

| Sampling Information | | | | |
|---|---|---|---|---|
| Serial Number | Anatomical Spatial Data | Angle | Parameter | Note |
| P1 | (X1, Y1, Z1) | α1 | C1 | Valid |
| P2 | (X2, Y2, Z2) | α1 | C2 | Invalid |
| P2 | (X2, Y2, Z2) | α2 | C2-1 | Valid |
| P3 | (X3, Y3, Z3) | α1 | C3 | Invalid |
| P3 | (X3, Y3, Z3) | α2 | C3-1 | Valid |
| P4 | (X4, Y4, Z4) | α1 | C4 | Valid |
| : | : | : | : | : |
| PN | (XN, YN, ZN) | α1 | CN | Valid |

| Surface Information | | | | |
|---|---|---|---|---|
| Serial Number | Anatomical Spatial Data | Angle | Parameter | Note |
| P1 | (X1, Y1, Z1) | α1 | C1 | Valid |
| P2 | (X2, Y2, Z2) | α2 | C2-1 | Valid |
| P3 | (X3, Y3, Z3) | α2 | C3-1 | Valid |
| P4 | (X4, Y4, Z4) | α1 | C4 | Valid |
| : | : | : | : | : |
| PN | (XN, YN, ZN) | α1 | CN | Valid |

(51) Int. Cl.
*A61B 17/17* (2006.01)
*A61B 34/00* (2016.01)
*A61B 34/20* (2016.01)
*A61B 90/00* (2016.01)
*A61B 34/30* (2016.01)

(52) U.S. Cl.
CPC ........ *A61B 34/74* (2016.02); *A61B 2034/105* (2016.02); *A61B 2034/107* (2016.02); *A61B 2034/2057* (2016.02); *A61B 2034/2065* (2016.02); *A61B 2034/2072* (2016.02); *A61B 2034/252* (2016.02); *A61B 2034/304* (2016.02); *A61B 2090/363* (2016.02); *A61B 2090/374* (2016.02); *A61B 2090/3762* (2016.02); *A61B 2090/3937* (2016.02); *A61B 2090/3966* (2016.02); *A61B 2090/3983* (2016.02); *A61B 2090/3995* (2016.02)

(58) Field of Classification Search
CPC ...... A61B 2034/107; A61B 2034/2057; A61B 2034/2065; A61B 2034/2072; A61B 2034/252; A61B 2090/363; A61B 2090/3983
See application file for complete search history.

(56) References Cited

U.S. PATENT DOCUMENTS

| | | | | |
|---|---|---|---|---|
| 6,006,126 A * | 12/1999 | Cosman | | A61B 34/20 600/414 |
| 6,033,415 A * | 3/2000 | Mittelstadt | | G06T 3/0006 128/922 |
| 6,166,809 A * | 12/2000 | Pettersen | | G01C 15/00 356/612 |
| 6,205,411 B1 * | 3/2001 | DiGioia, III | | A61F 2/46 703/11 |
| 6,236,875 B1 * | 5/2001 | Bucholz | | A61B 5/0064 600/407 |
| 6,381,485 B1 * | 4/2002 | Hunter | | G06T 3/0068 324/244 |
| 6,430,434 B1 * | 8/2002 | Mittelstadt | | A61B 17/175 600/426 |
| 7,570,791 B2 * | 8/2009 | Frank | | A61B 6/463 382/128 |
| 7,835,778 B2 * | 11/2010 | Foley | | A61B 17/1757 600/407 |
| 8,358,818 B2 * | 1/2013 | Miga | | A61B 90/36 382/128 |
| 8,615,286 B2 | 12/2013 | Shen et al. | | |
| 8,781,186 B2 * | 7/2014 | Clements | | A61B 34/20 382/128 |
| 8,996,169 B2 * | 3/2015 | Lightcap | | A61B 34/20 700/250 |
| 9,081,863 B2 * | 7/2015 | Error | | G06F 16/248 |
| 9,345,552 B2 * | 5/2016 | Janik | | A61B 17/16 |
| 9,603,665 B2 * | 3/2017 | Bowling | | A61B 34/30 |
| 9,636,185 B2 * | 5/2017 | Quaid | | A61B 17/1764 |
| 9,993,305 B2 * | 6/2018 | Andersson | | A61B 34/10 |
| 10,219,811 B2 * | 3/2019 | Haider | | A61B 34/76 |
| 10,347,380 B2 * | 7/2019 | Miller | | G06T 7/337 |
| 10,420,616 B2 * | 9/2019 | Kostrzewski | | G06T 7/33 |
| 10,644,680 B1 * | 5/2020 | Paraschou | | H03K 5/1565 |
| 10,878,174 B1 * | 12/2020 | Vontobel | | G06N 5/04 |
| 10,945,795 B2 * | 3/2021 | Andersson | | A61B 17/1757 |
| 10,987,176 B2 * | 4/2021 | Poltaretskyi | | A61B 5/7282 |
| 11,071,594 B2 * | 7/2021 | Kostrzewski | | A61B 17/1703 |
| 11,116,574 B2 * | 9/2021 | Haider | | A61B 34/10 |
| 2003/0225415 A1 * | 12/2003 | Richard | | A61B 90/36 606/102 |
| 2004/0024311 A1 * | 2/2004 | Quaid, III | | A61B 17/1703 600/428 |
| 2005/0113659 A1 | 5/2005 | Pothier et al. | | |
| 2006/0040233 A1 | 2/2006 | Weinstein et al. | | |
| 2006/0142657 A1 * | 6/2006 | Quaid | | A61F 2/30942 600/424 |
| 2006/0240379 A1 | 10/2006 | Weinstein | | |
| 2007/0142751 A1 * | 6/2007 | Kang | | A61B 34/10 600/587 |
| 2008/0004633 A1 * | 1/2008 | Arata | | A61B 17/1764 606/130 |
| 2008/0077158 A1 * | 3/2008 | Haider | | A61B 17/1703 606/130 |
| 2008/0255442 A1 * | 10/2008 | Ashby | | A61B 90/36 600/407 |
| 2011/0019893 A1 * | 1/2011 | Rahn | | A61B 18/1492 382/131 |
| 2011/0112397 A1 * | 5/2011 | Shen | | A61B 34/20 600/424 |
| 2012/0041446 A1 * | 2/2012 | Wong | | A61F 2/3859 606/96 |
| 2013/0211791 A1 | 8/2013 | Tsai et al. | | |
| 2013/0317363 A1 * | 11/2013 | Case | | A61B 8/4263 600/439 |
| 2013/0345718 A1 * | 12/2013 | Crawford | | A61B 17/025 606/130 |
| 2014/0121676 A1 * | 5/2014 | Kostrzewski | | A61B 34/30 606/130 |
| 2014/0206990 A1 | 7/2014 | Epstein et al. | | |
| 2014/0372138 A1 * | 12/2014 | Chari | | G06F 19/00 705/2 |
| 2015/0220682 A1 | 8/2015 | Netravali et al. | | |
| 2016/0354162 A1 * | 12/2016 | Yen | | A61B 17/1671 |
| 2018/0096485 A1 | 4/2018 | Held | | |
| 2018/0235715 A1 | 8/2018 | Amiot et al. | | |
| 2018/0263714 A1 * | 9/2018 | Kostrzewski | | A61B 34/30 |
| 2018/0279993 A1 | 10/2018 | Crawford et al. | | |
| 2020/0038108 A1 * | 2/2020 | Chou | | A61B 34/74 |
| 2020/0388085 A1 * | 12/2020 | Furnstahl | | A61B 17/848 |

FOREIGN PATENT DOCUMENTS

| | | |
|---|---|---|
| CN | 104334100 A | 2/2015 |
| CN | 104507410 A | 4/2015 |
| CN | 105825752 A | 8/2016 |
| CN | 105142549 B | 1/2018 |
| CN | 107669338 A | 2/2018 |
| EP | 1879499 A2 | 1/2008 |
| EP | 3360502 A2 | 8/2018 |
| JP | 2002524192 A | 8/2002 |
| JP | 2005515017 A | 5/2005 |
| JP | 2008538184 A | 10/2008 |
| JP | 2009537230 A | 10/2009 |
| JP | 2017113343 A | 6/2017 |
| JP | 2017119112 A | 7/2017 |
| JP | 2019107451 A | 7/2019 |

* cited by examiner

| Sampling Information | | | | |
|---|---|---|---|---|
| Serial Number | Anatomical Spatial Data | Angle | Parameter | Note |
| P1 | (X1, Y1, Z1) | α1 | CI1 | Valid |
| P2 | (X2, Y2, Z2) | α1 | CI2 | Invalid |
| P2 | (X2, Y2, Z2) | α2 | CI2-1 | Valid |
| P3 | (X3, Y3, Z3) | α1 | CI3 | Invalid |
| P3 | (X3, Y3, Z3) | α2 | CI3-1 | Valid |
| P4 | (X4, Y4, Z4) | α1 | CI4 | Valid |
| ⋮ | ⋮ | ⋮ | ⋮ | ⋮ |
| PN | (XN, YN, ZN) | α1 | CIN | Valid |

| Surface Information | | | | |
|---|---|---|---|---|
| Serial Number | Anatomical Spatial Data | Angle | Parameter | Note |
| P1 | (X1, Y1, Z1) | α1 | CI1 | Valid |
| P2 | (X2, Y2, Z2) | α2 | CI2-1 | Valid |
| P3 | (X3, Y3, Z3) | α2 | CI3-1 | Valid |
| P4 | (X4, Y4, Z4) | α1 | CI4 | Valid |
| ⋮ | ⋮ | ⋮ | ⋮ | ⋮ |
| PN | (XN, YN, ZN) | α1 | CIN | Valid |

SURGERY ASSISTIVE SYSTEM AND METHOD FOR OBTAINING SURFACE INFORMATION THEREOF

FIELD

The present disclosure relates to a surgery assistive system, and more particularly to a method for registration that enhances accuracy and precision of computer-assisted surgeries performed by the surgery assistive system.

BACKGROUND

Numerous surgical operations require high manual precision on the part of the surgeon. For example, surgical orthopedic operations require the surgeon to mill, drill or saw a bone of a subject at a precise location and at a precise angle in order to fit a given implant into the bone or to shape the bone to create a desired geometric profile. Such operations are usually performed by free-hand, with the surgeon holding a specific surgical instrument and following a trajectory based on anatomical landmarks. Accuracy of the surgical operations is thus dependent on the skill of the surgeon in following the predetermined plan with the hand-held surgical instrument.

Taking the advantages of information technology and robotics, computer assisted surgery has offered a reliable option in improving the accuracy and precision of surgical operations. Computer assisted surgery represents a surgical concept that utilizes computer technology to visualize operating fields in a preoperative virtual environment to allow a more accurate preoperative diagnostic and well-defined surgical planning. In computer assisted surgeries, patient registration is a critical preoperative procedure that correlates positions of a virtual three-dimensional (3D) dataset gathered by computer medical imaging, such as computed tomography (CT) or magnetic resonance imaging (MRI), with positions of the patient. Patient registration eliminates the necessity of maintaining the patient in the same strict position during both preoperative scanning and surgery, and ensures geometrical accuracy of surgical operations.

Conventional registration method primarily includes fiducial registration and surface matching registration. Fiducial registration registers a specific anatomical region to the computer assisted navigation system by detecting a plurality of fiducial markers that are attached onto anatomical landmarks to define the anatomical region. Surface matching registration is performed by utilizing mechanical or ultrasound probes to identify the coordinates of a set of points on an anatomical surface structure of an operating field, thus offering higher accuracy in spatial recognition and reduced surgical invasiveness over fiducial registration.

In conventional surface matching registration, the probe may be coupled to a sensor to detect the mechanical contact of the probe with the anatomical surface. For example, Shen et al. discloses in U.S. Pat. No. 8,615,286 a device and method for finding the location of a bone surface in patients that utilizes a force sensor installed at the base of a thin probe to detect resistance of the material encountered by the probe to discriminate engagement of the probe with bone or soft tissues or with different types of tissue with dissimilar hardness.

However, in actual surgical operations, the conventional thin probe tends to slip off the intended surface of contact due to the lack of control over the precise contact angle of the probe or the varying hardness between different layers of tissues, therefore resulting in significant reduction in accuracy of the registration. None of the existing art provides a mean that can control the angle of contact of the probe on the anatomical surface or determine the validity of the mechanical contact between the probe and the surface.

BRIEF SUMMARY OF THE DISCLOSURE

An objective of the present disclosure is to provide a surgical instrument that controls and detects the angle of contact of a registration probe thereof on an anatomical surface.

Another objective of the present disclosure is to provide a registration method for the surgical instrument that validates the mechanical contact between the registration probe and the anatomical surface.

An embodiment of the present disclosure provides a surgery assistive system. The system includes an instrument having a tool and a manipulator connected to the tool, a spatial sensor system for detecting spatial information of the tool, and a computer system electrically connected to the instrument, the spatial sensor system, and a user interface, for manipulating a kinematic state of the manipulator according to the spatial information of the tool as detected by the spatial sensor system.

In a preferred embodiment, the instrument of the surgery assistive system further includes a force sensor for detecting force and/or torque sustained by the tool.

In a preferred embodiment, the force sensor is disposed between the tool and the manipulator and/or disposed in the tool.

In a preferred embodiment, parameters associated with the contact include a force sustained by the tool, a torque sustained by the tool, an output power of a plurality of actuators of the manipulator, and a duration of steady contact between the tool and one of the sampling points.

Another embodiment of the present disclosure provides a method for obtaining surface information for registration by the surgery assistive system. The method includes the steps of: (S1) defining, by the computer system, a target region and a plurality of reference points in the target region on a virtual anatomical model of a subject; (S2) prompting, via the user interface, a user to generate sampling information by using the instrument to sample a plurality of sampling points on the subject corresponding to the reference points, wherein each piece of the sampling information comprises a coordinate of one of the sampling points, an angle of a contact of the tool at the one of the sampling points as detected by the spatial sensor system, and parameters associated with the contact; and (S3) designating, by the computer system, the sampling information as surface information of the sampling points.

In a preferred embodiment, the sampling points are sampled by allowing the computer system to manipulate the kinematic state of the manipulator so as to control a tip of the probe to contact the sampling points one at a time.

In a preferred embodiment, before the step of S1, the method further includes the steps of: defining, by the computer system, a plurality of matching reference points in the target region on the virtual anatomical model; prompting, via the user interface, the user to generate matching spatial data by using the instrument to sample a plurality of matching points on the subject corresponding to the matching reference points; and assigning, by the computer system, the matching spatial data into the virtual anatomical model.

In a preferred embodiment, the matching sampling points are sampled by allowing the computer system to manipulate the kinematic state of the manipulator so as to control a tip of the probe to contact the matching points one at a time.

In a preferred embodiment, after the step of S2, the method further includes the steps of: (S21) validating a current piece of the sampling information; (S22) checking sampling status; and (S23) filtering the sampling information.

In a preferred embodiment, the step of (S21) comprises steps of: (S211) determining if the parameters included in the current piece of the sampling information meets at least one sampling criterion; (S212) denoting the current piece of the sampling information with a first note if the parameters meet the sampling criterion, or denoting the current piece of the sampling information with a second note if the parameters do not meet the sampling criterion; and (S213) proceeding to the Step of S22 when the current piece of the sampling information is denoted the first note, or proceeding to the Step of S2 when the current piece of the sampling information is denoted the second note.

In a preferred embodiment, the sampling criterion comprises a force sustained by the tool being equal to or stronger than a force threshold value, a torque sustained by the tool being equal to or smaller than a torque threshold value, an output power of a plurality of actuators of the manipulator being equal to or higher than a power threshold value, and/or a duration of steady contact between the tool and one of the sampling points being equal to or longer than a time threshold.

In a preferred embodiment, the step of (S22) includes the steps of: (S221) determining if sampling information of all of the sampling points are denoted a first note; and (S222) proceeding to the Step of S23 if the sampling information of all of the sampling points have been sampled, or proceeding to the Step of S2 if at least one of the sampling information of all of the sampling points have not been sampled.

In a preferred embodiment, the step S23 is performed by separating sampling information denoted the second note from all of the sampling information being denoted a first note.

In a preferred embodiment, after the step of S3, the method further include the steps of: (S4) assigning the surface information into the virtual anatomical model to register the virtual anatomical model into a coordinate system; (S5) refining the virtual anatomical model according to the surface information; and (S6) updating a surgical plan according to the surface information and the refined virtual anatomical model.

According to the various embodiments of the present disclosure, the surgery assistive system provides an accurate and efficient method for registration. The method defines a target region on a surface of a subject and a set of reference points distributed in the target region that cover a plurality of surface features of the surface, and validates the mechanical contacts between the probe of the surgical instrument and the surface, therefore effectively improving the accuracy and precision of computer-assisted surgeries.

BRIEF DESCRIPTION OF THE DRAWINGS

The accompanying drawings illustrate one or more embodiments of the present disclosure and, together with the written description, explain the principles of the present disclosure. Wherever possible, the same reference numbers are used throughout the drawings to refer to the same or like elements of an embodiment.

FIG. 16 is an example of filtering sampling information to obtain surface information for registration of the surgery assistive system in accordance with an embodiment of the present disclosure.

In accordance with common practice, the various described features are not drawn to scale and are drawn to emphasize features relevant to the present disclosure. Like reference characters denote like elements throughout the figures and text.

DETAILED DESCRIPTION OF THE PREFERRED EMBODIMENTS

Figure 1:
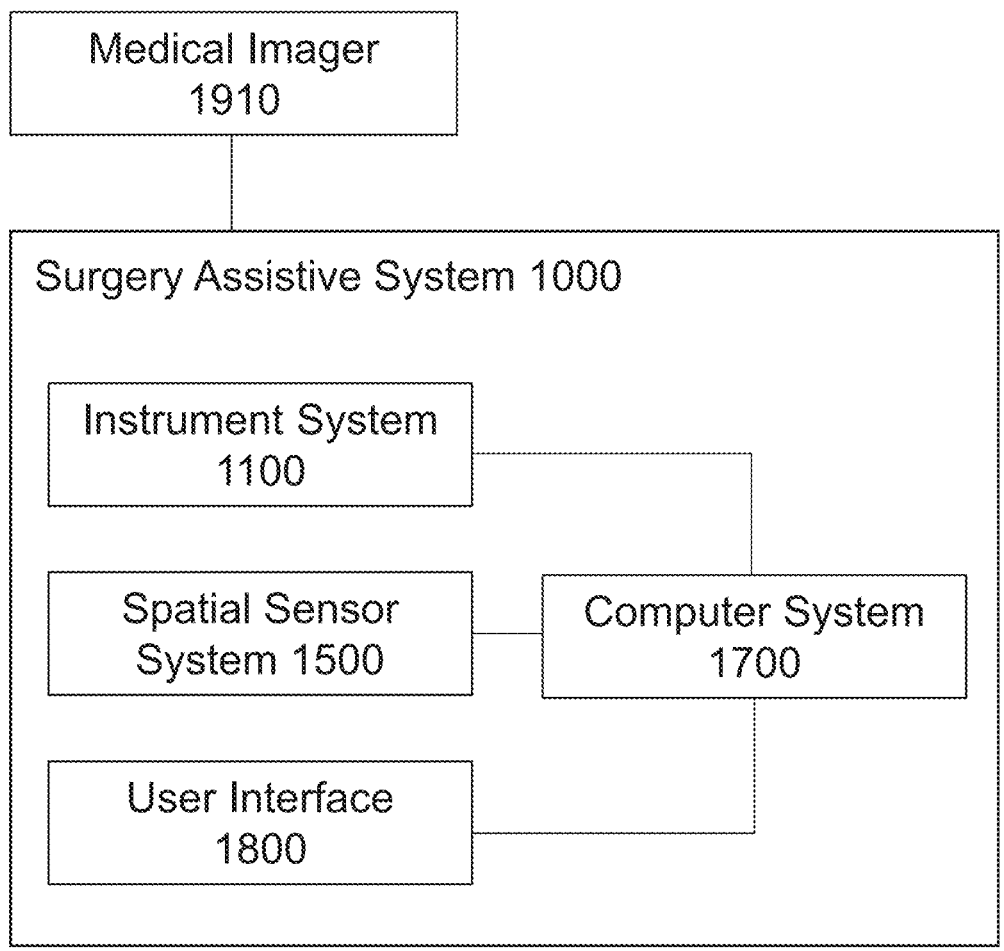
FIG. 1 is a block diagram of a surgery assistive system in accordance with an embodiment of the present disclosure.

The present disclosure will now be described more fully hereinafter with reference to the accompanying drawings illustrating various exemplary embodiments of the disclosure. The present disclosure may, however, be embodied in many different forms and should not be construed as limited to the embodiments set forth herein. Rather, these embodiments are provided so that this disclosure will be thorough and complete, and will fully convey the scope of the disclosure to those skilled in the art. Like reference numerals refer to like elements throughout.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," or "includes" and/or "including" or "has" and/or "having" when used herein, specify the presence of stated features, regions, integers, steps, operations, elements, and/or components, but do not preclude the presence or addition of one or more other features, regions, integers, steps, operations, elements, components, and/or groups thereof.

It will be understood that the terms "and/or" and "at least one" include any and all combinations of one or more of the associated listed items. It will also be understood that, although the terms first, second, third etc. may be used herein to describe various elements, components, regions, parts and/or sections, these elements, components, regions, parts and/or sections should not be limited by these terms. These terms are only used to distinguish one element, component, region, part or section from another element, component, region, layer or section. Thus, a first element, component, region, part or section discussed below could be termed a second element, component, region, layer or section without departing from the teachings of the present disclosure.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Figure 2:
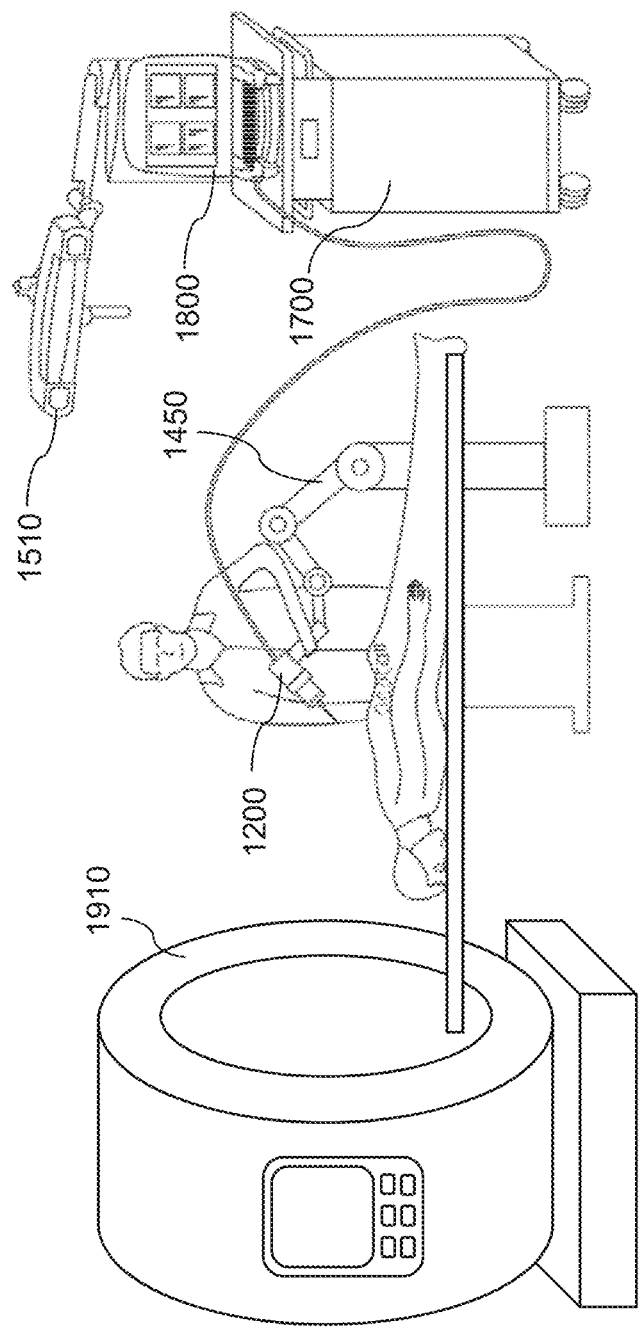
FIG. 2 is a schematic illustration of the surgery assistive system in accordance with an embodiment of the present disclosure.

Referring now to FIG. 1 and FIG. 2. According to an embodiment of the present disclosure, a surgery assistive system 1000 for pre-surgical and surgical operations includes surgical hardware coupled with electronic modules and processor-executable instructions. The surgery assistive system 1000 includes an instrument system 1100, a spatial sensor system 1500, a user interface 1800, and a computer system 1700 electrically connected to the instrument system 1100, the spatial sensor system 1500, and the user interface 1800. In the embodiment, the surgery assistive system 1000 allows a user (e.g., a surgeon) to conduct surgery on a subject (e.g., a patient) by the instrument system 1100 with reference to the user interface 1800. At least one medical imager 1910 is in communication with the surgery assistive system 1000 and is configured to acquire medical images of the subject and transmit the images to the surgery assistive system 1000. The spatial sensor system 1500 is configured to generate spatial information of the subject and the environment. The computer system 1700 is configured to generate a virtual anatomical model according to the medical images and a surgical plan according to the virtual anatomical model, to track the surgical environment according to the spatial information received from the spatial sensor system 1500, and to control movement or alter the kinematic state of the manipulator 1210. The user interface 1800 visualizes the anatomical model and allows the user to navigate through the operating field according to the surgical plan.

As illustrated in FIG. 2, the instrument system 1100 of the surgery assistive system 1000 includes a hand-held instrument 1200 for performing surgery on the subject. In the embodiment, the instrument system 1100 may further include a support arm 1450 connected to the instrument 1200 to reduce weight load on the hands of the user and optionally provide more operational stability during surgeries.

Figure 3:
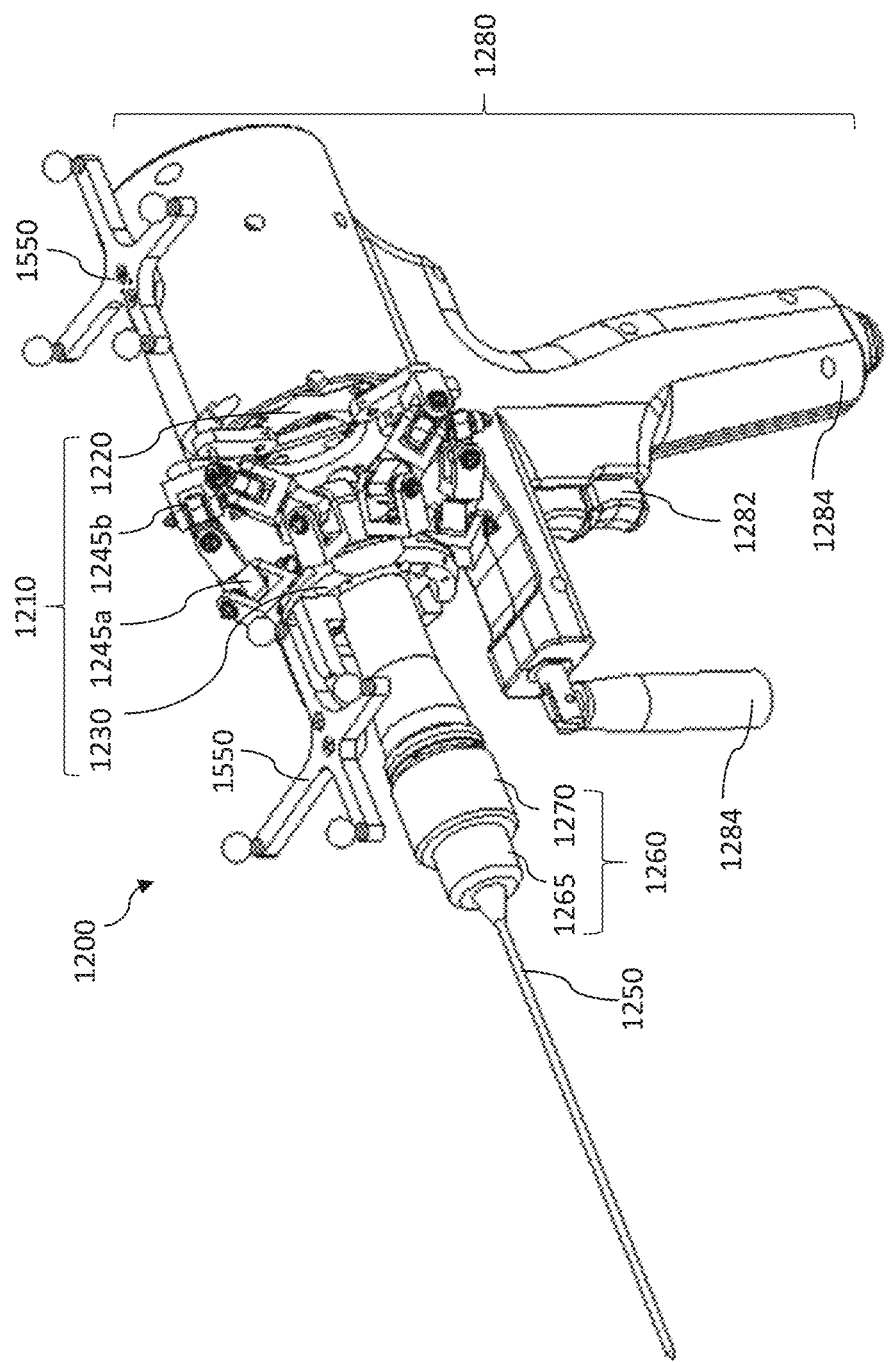
FIG. 3 is a perspective view of a hand-held instrument of the surgery assistive system in accordance with an embodiment of the present disclosure.
Figure 4:
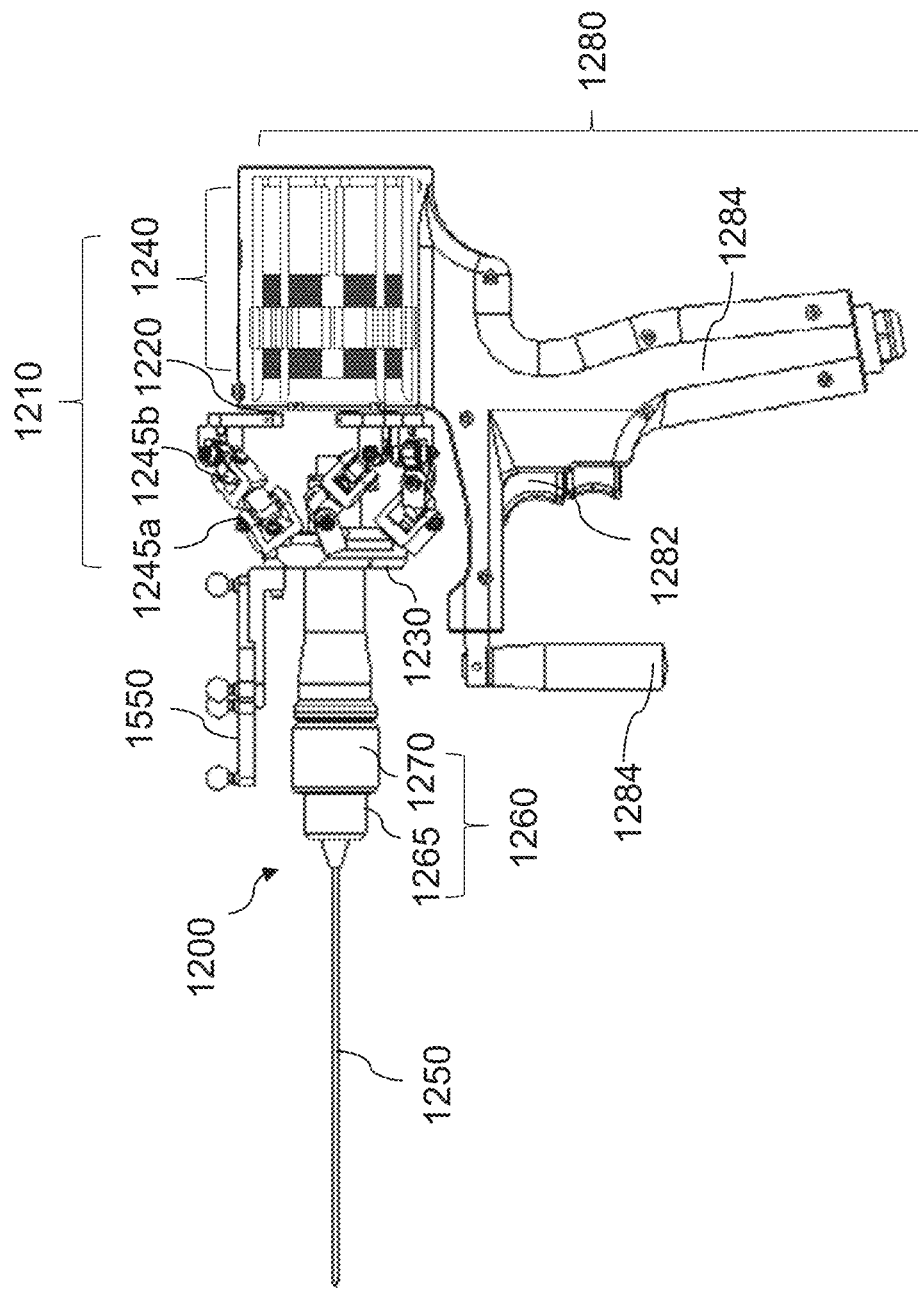
FIG. 4 is a side view of the hand-held instrument of the surgery assistive system in accordance with an embodiment of the present disclosure.

Referring to FIG. 3 and FIG. 4. According to an embodiment, the hand-held instrument 1200 includes a tool 1250, a tool installation base 1260, a manipulator 1210, and an instrument housing 1280. The tool 1250 is configured to contact or modify an anatomical surface on a body part of the subject. The tool installation base 1260 is connected to an end of the tool 1250 and the manipulator 1210 so that the tool 1250 is stably connected to the manipulator 1210. The manipulator 1210 is a mechanism controlled by the computer system 1700 for manipulating the position and orientation of the tool 1250. The instrument housing 1280 is connected to the manipulator 1210 to accommodate at least a portion of the manipulator 1210 and provide one or more handles 1284 for allowing the user to hold onto and maneuver the instrument 1200 during operation of the surgery assistive system.

In the embodiment, the tool 1250 may be a probe or indicator for contacting or assessing an anatomical site of the subject and detecting the structure or status of the anatomical site. The tool 1250 may be a drill bit, bur, curette, saw, screwdriver or other tool commonly used in surgical medicine that modifies or removes a portion of the tissues at the anatomical site by drilling, milling, cutting or scraping. In some embodiments, the tool 1250 is a mechanical, optical or ultrasound probe for performing surface matching registration and may be, but is not limited to, a rigid probe, a pressure sensor, a piezoelectric sensor, an elastomeric sensor, an optical camera, a laser scanner or an ultrasonic scanner.

Figure 5:
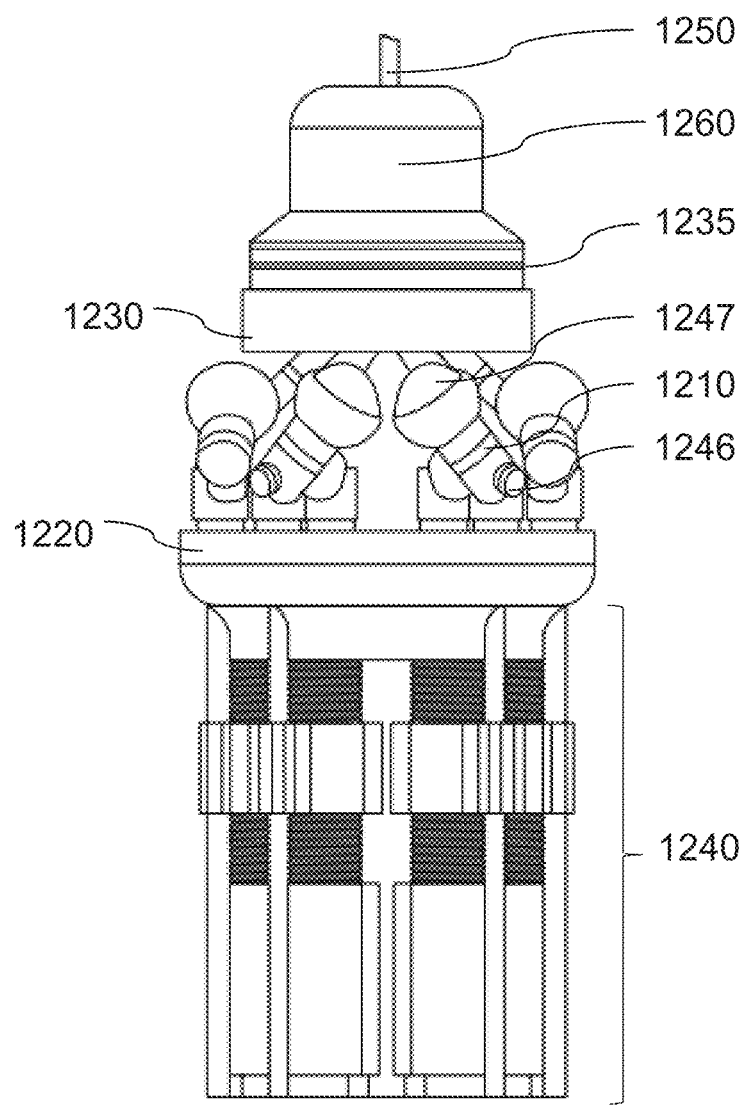
FIG. 5 is a side view of a manipulator of the hand-held instrument of the surgery assistive system in accordance with an embodiment of the present disclosure.
Figure 6:
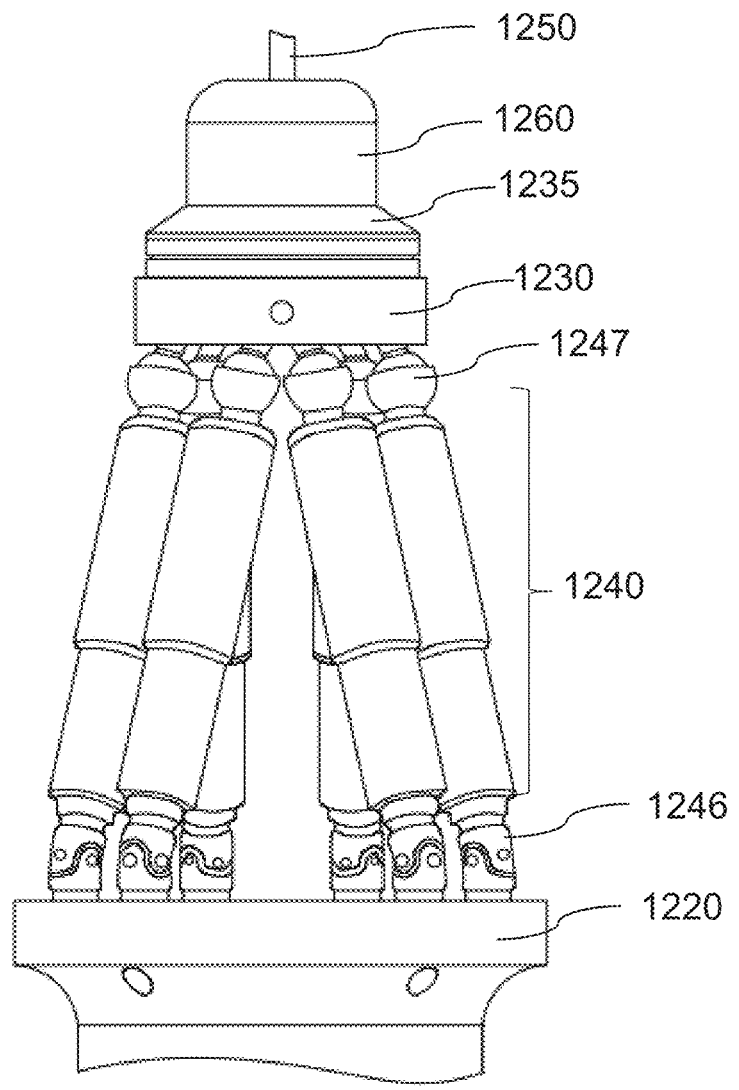
FIG. 6 is a side view of another manipulator of the hand-held instrument of the surgery assistive system in accordance with an embodiment of the present disclosure.

In the embodiment, the tool installation base 1260 is connected to the tool 1250 and a first side of a robotically controlled platform 1230 of the manipulator 1210. The tool installation base 1260 includes a tool adaptor 1265 and a motor 1270 connected to the tool adaptor 1265. The tool adaptor 1265 may be a clamp or other fastening structure for holding an end of the tool 1250 firmly to avoid displacement of the tool during operations. The motor 1270 may be a direct current (DC) motor or an alternating current (AC) motor for transducing electric energy into mechanical energy and generating a linear or rotary force to drive movement of the tool 1250. In an alternative embodiment, the motor may be disposed at the rear end of the instrument to reduce loading on the manipulator 1210 during operation of the instrument and to redistribute the weight of the instrument 1200 for improved user ergonomics. Additionally, as illustrated in FIG. 5 and FIG. 6, the tool installation base 1260 may further include a force sensor 1235 connected to the first side of the platform 1230 for detecting the force and/or torque sustained by the tool 1250 during surgeries. In other embodiments, the force sensor 1235 may be disposed in the probe or tool of the instrument; alternatively, the instrument 1200 may further include another force sensor (not shown in figures) disposed in the probe or tool. The force sensor may be, but is not limited to, a strain gauge, a force-sensitive resistor, a pressure transducer, a piezoelectric sensor, an electroactive polymer or an optical fiber bending sensor.

In the embodiment, the manipulator 1210 includes a base 1220, the platform 1230 connected to the tool installation base 1260, a plurality of joints 1245a, 1245b mounted on a second side of the platform 1230 away from the tool 1250 and on a first side of the base 1220 facing the platform 1230, and a plurality of actuators 1240 connected to the base 1220 on a second side of the base 1220 away from the platform 1230. As illustrated in FIG. 4, the base 1220 may be immobilized on or accommodated in the instrument housing 1280. The manipulator 1210 may be a parallel manipulator, such as a Stewart manipulator with six degrees of freedom (DOFs), for higher space efficiency and maneuverability. Additionally, the manipulator is preferably made of stainless steel or carbon fiber and arranged in a specific mechanical structure that allows the manipulator 1210 to possess sufficient sustainability against the force and/or torque generated from the tool 1250 contacting the subject during surgeries.

In the embodiment, the joints of the manipulator 1210 may be, but are not limited to, revolute joints, prismatic joints, spherical joints, universal joints, cylinder joint, or any combination thereof that enables a desired DOF. As exemplified in FIG. 5 and FIG. 6, the manipulator 1210 having a general Stewart platform with six DOFs may include universal joints 1246 and spherical joints 1247 to enable broad ranges of motion and various kinematic states of the manipulator 1210. The manipulator 1210 may further include a plurality of connectors, each being connected to one of the joints 1245*a* and one of the joints 1245*b*, to enable a broader range of movement of the tool 1250.

In the embodiment, the actuators 1240 of the manipulator 1210 connected to the base 1220 on the side opposite to the joints are configured to drive the joints, and the connectors if any, to move according to control signals transmitted from the computer system 1700. In an alternative embodiment, the actuators 1240 and the joints may be disposed on the same side of the base 1220. As exemplified in FIG. 6, the actuators 1240 are disposed between the base 1220 and the platform 1230, with each of the actuators 1240 being joined by a universal joint 1246 and a spherical joint 1247. The plurality of actuators 1240 may be linear actuators for higher precision and stronger sustainability.

Referring again to FIG. 3 and FIG. 4. In the embodiment, in addition to accommodating the manipulator 1210 and providing handles, the instrument housing 1280 may further include a control module 1282 for allowing the user to trigger, halt, or adjust actions of the tool 1250 or perform other functions of the instrument 1200.

In the embodiment, the hand-held instrument 1200 may be used with a calibration device 1300 configured to calibrate kinematic state of the manipulator 1210 in respect of the instrument housing 1280 so as to ensure geometric accuracy of the instrument 1200.

In the embodiment, the instrument 1200 may include at least one inertial measurement unit that detects acceleration, velocity, displacement, angular velocity and/or angular acceleration of the instrument 1200.

Figure 7:
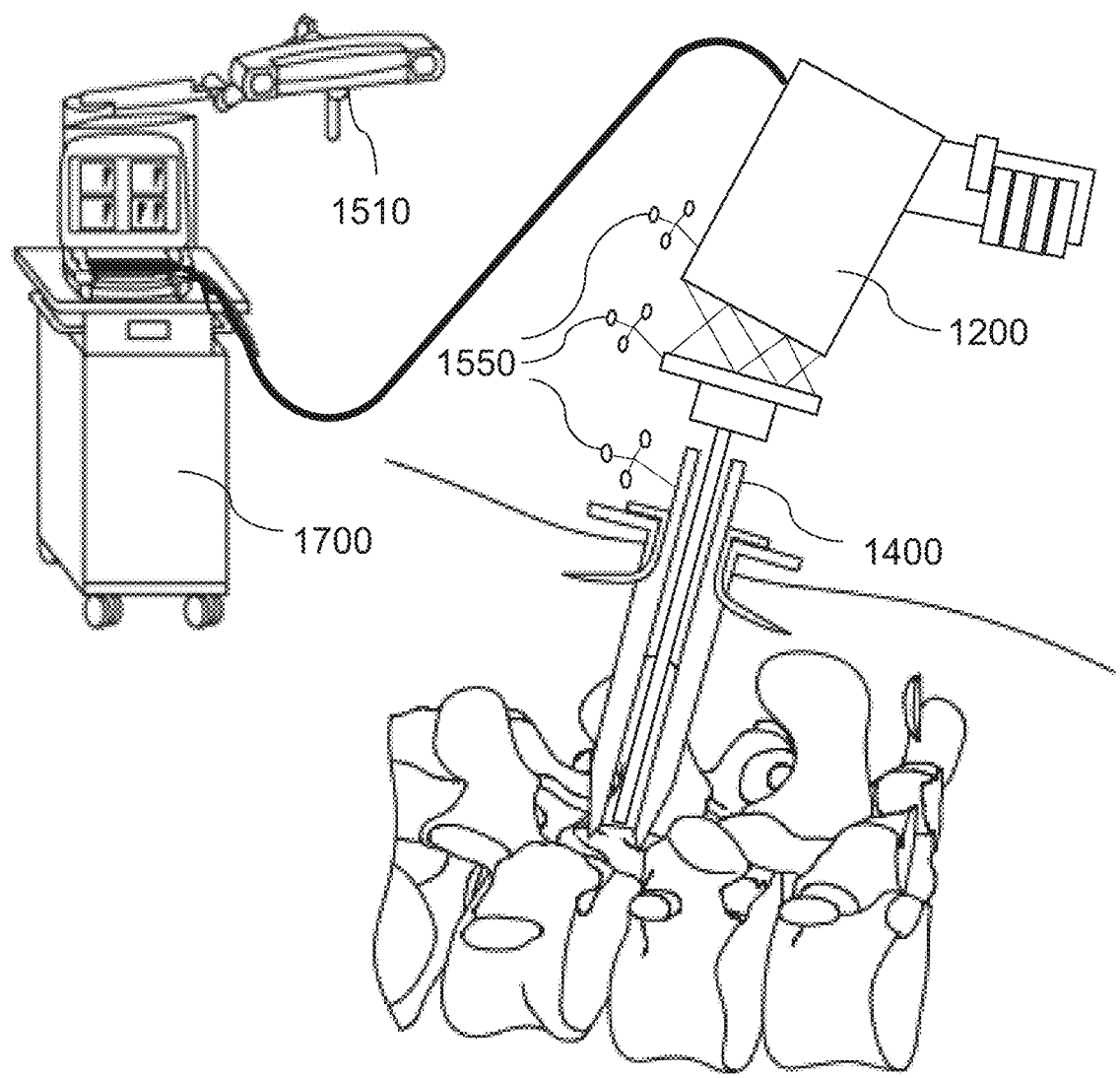
FIG. 7 is a schematic illustration of an operation state of the surgery assistive system in accordance with an embodiment of the present disclosure.

Referring to FIG. 7. The instrument 1200 may be used with a trocar 1400, especially in a minimally invasive surgery, to provide a physical portal for the tool 1250 of the instrument 1200 to reach the anatomical site of interest. In an alternative embodiment, the trocar 1400 may be removably connected to the platform 1230 of the manipulator 1210 to enable simultaneous entry of the trocar 1400 and the tool 1250 into the anatomical site.

Figure 8:
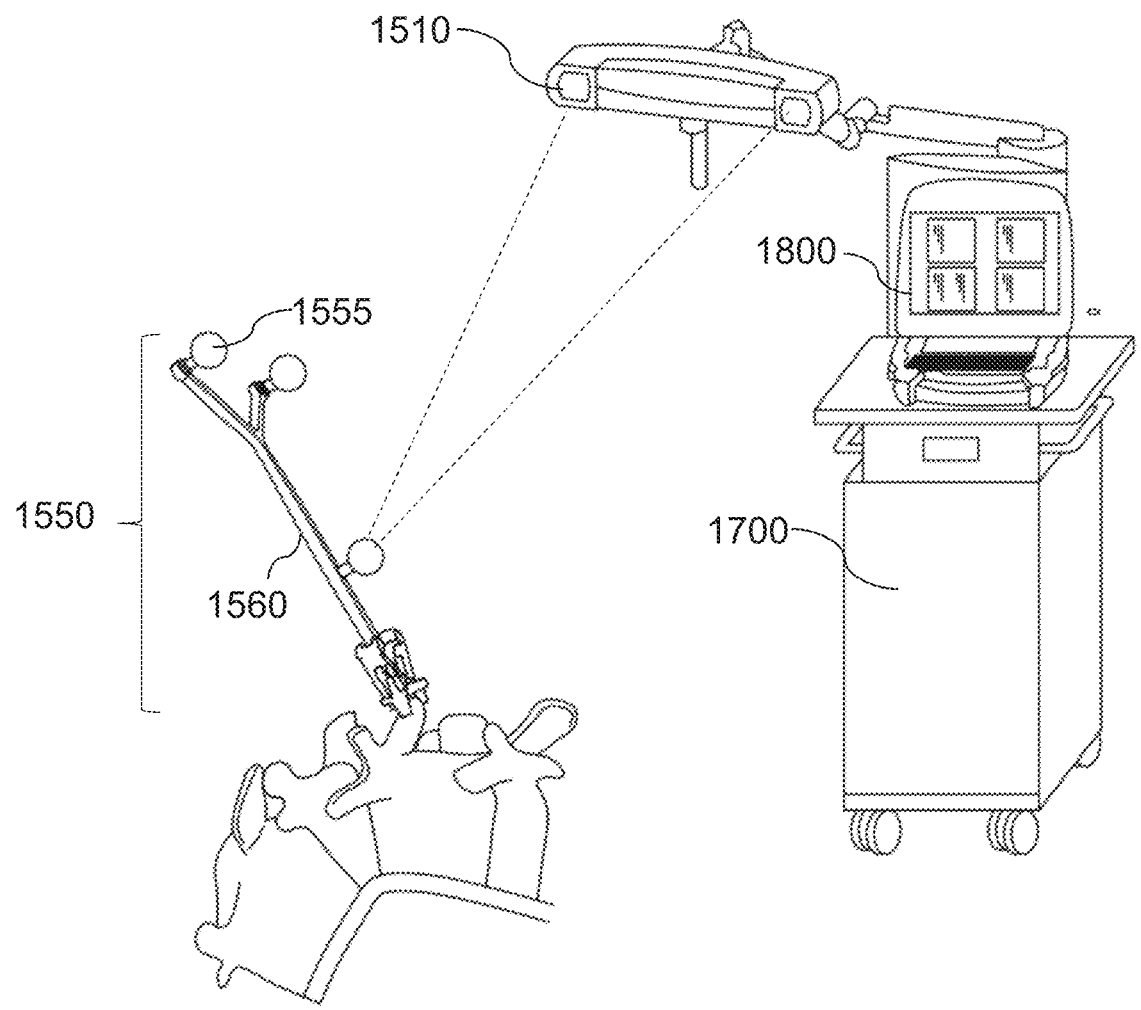
FIG. 8 is a schematic illustration of an operation state of a spatial sensor system of the surgery assistive system in accordance with an embodiment of the present disclosure.

Referring now to FIG. 8. According to an embodiment of the present disclosure, the spatial sensor system 1500 of the surgery assistive system 1000 is configured to detect and thus enable tracking of the spatial information (e.g., location and orientation) of at least one target object, and includes at least one spatial marker frame 1550 removably attached to the target object, and a spatial sensor 1510 having at least one camera for receiving signals transmitted from the spatial marker frame 1550.

As exemplified in FIG. 7 and FIG. 8, the target object may be the instrument 1200, the trocar 1400, or a selected anatomical site. In the embodiment, the spatial marker frame 1550 includes a plurality of markers 1555 for emitting electromagnetic signals, sound wave, heat, or other perceivable signals, and an adaptor 1560 removably attached to the target object for holding the markers 1555 so that the target object becomes trackable by the spatial sensor 1510. In another embodiment, the spatial sensor system 1500 may further include a signal generator (not shown in figure) disposed on the spatial sensor 1510 or at a predefined location. Consequently, signal transmission by the markers 1555 may be active or passive; in other words, the signals emitted by the markers 1555 may be generated by the marker spheres, or the markers 1555 may be covered with reflective material so that signals generated by the signal generator are reflected by the markers 1555 to the spatial sensor 1510.

In the embodiment, the signal received by the spatial sensor 1510 is transmitted to the computer system 1700 and transformed into a coordinate system of the detected space and spatial information of the target object by triangulation or other transformation algorithm. Further, the markers 1555 of the spatial marker frame 1550 may be arranged on the adaptor 1560 in a specific pattern, as exemplified in FIG. 8, thus allowing the computer system 1770 to generate orientation information of the target object accordingly. The computer system 1700 may generate control signals according to the spatial and orientation information to control movement or alter kinematic state of the manipulator 1210 of the instrument 1200 or generate instructions to be shown on the user interface 1800 to prompt the user to move the instrument 1200 to a designated location or orientation.

According to an embodiment of the present disclosure, the computer system 1700 of the surgery assistive system 1000 includes a processor and a storage unit. The processor may be a general purpose processor, an application-specific instruction set processor or an application-specific integrated circuits that performs operations on a data source, such as the storage unit or other data stream. For example, the processor is an ARM based processor or an 8086x processor. In some embodiments, the processor further includes a plurality of digital or analog input/output, and may be a real-time operating system (RTOS) processor. The storage unit may store digital data assigned by the processor for immediate use in the computer system. The storage unit may be volatile, such as flash memory, read-only memory (ROM), programmable read-only memory (PROM), and erasable programmable read-only memory (EPROM), or non-volatile, such as dynamic random access memory (DRAM) and static random access memory (SRAM).

According to an embodiment, the user interface 1800 includes at least one output device for presenting information to the user and at least one input device. The information presented by the user interface 1800 may include, but is not limited to, surgical plans, two-dimensional (2D) or 3D reconstruction images, 2D or 3D drilling status (e.g., position, angle, depth or bending of the tool), compensation range of the tool, user guidance, warning area, notification of tool deviation from the surgical plan and notification of force sustainability limit of the tool. The output device may be a display, a light indicator or other visual means; alternatively, the output device may also be, or further include, a speech synthesizer or other audio means. The input device is capable of transducing commands entered by the user into electrical signals, and may be a pedal, a keyboard, a mouse, a touch panel, a voice recognition interface, or a gesture recognition interface.

Figure 9:
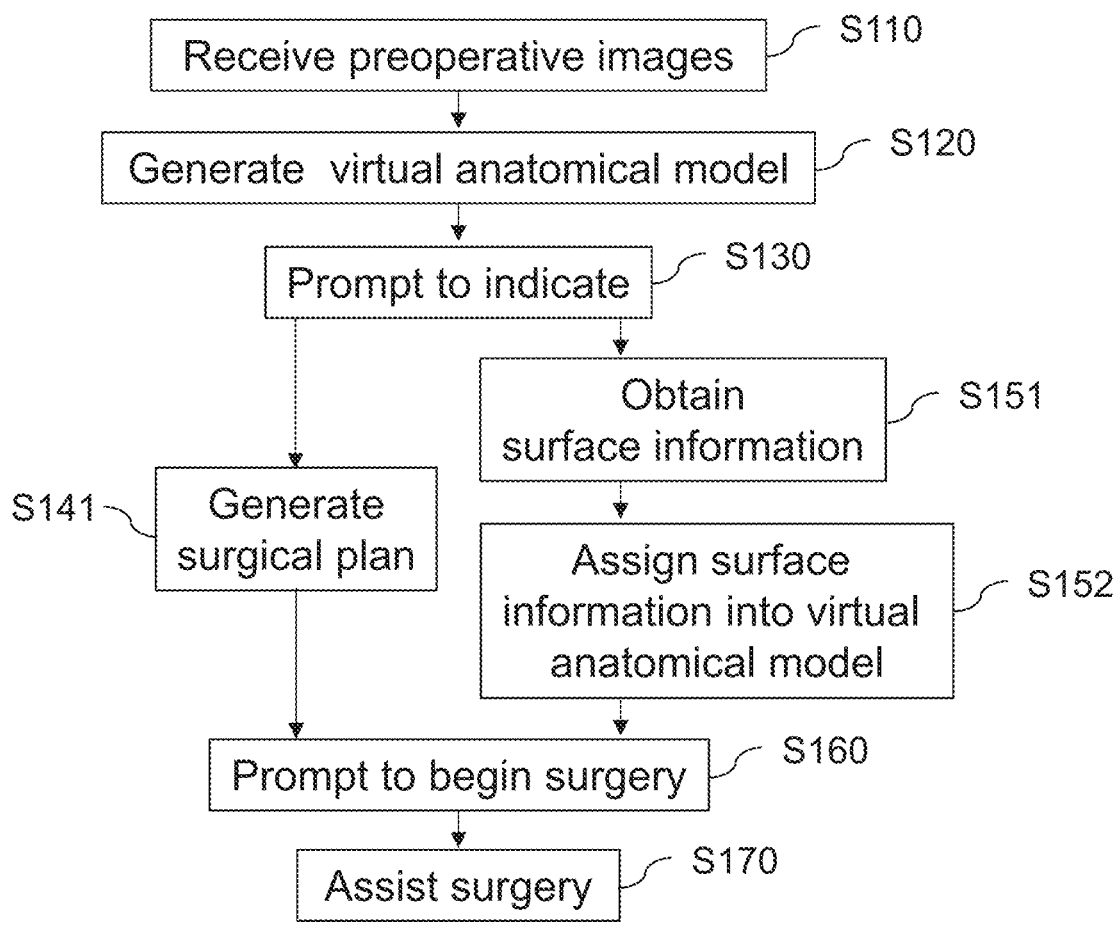
FIG. 9 is a flow diagram of an operation method of the surgery assistive system in accordance with an embodiment of the present disclosure.

Referring to FIG. 9. According to an embodiment of the present disclosure, a method of performing a computer-assisted surgery by the surgery assistive system 1000 includes the steps of: (S110) receiving a plurality of medical images from the medical imager 1910; (S120) generating a three-dimensional virtual anatomical model according to the medical images; (S130) prompting the user to indicate location(s) of interest on the virtual anatomical model; (S141) generating a surgical plan according to the virtual anatomical model, the indicated location(s), and physiological and/or pathological information obtained from the medical images; (S160) prompting the user to begin surgery according to the surgical plan; and (S170) assisting the user during the surgery.

Figure 10:
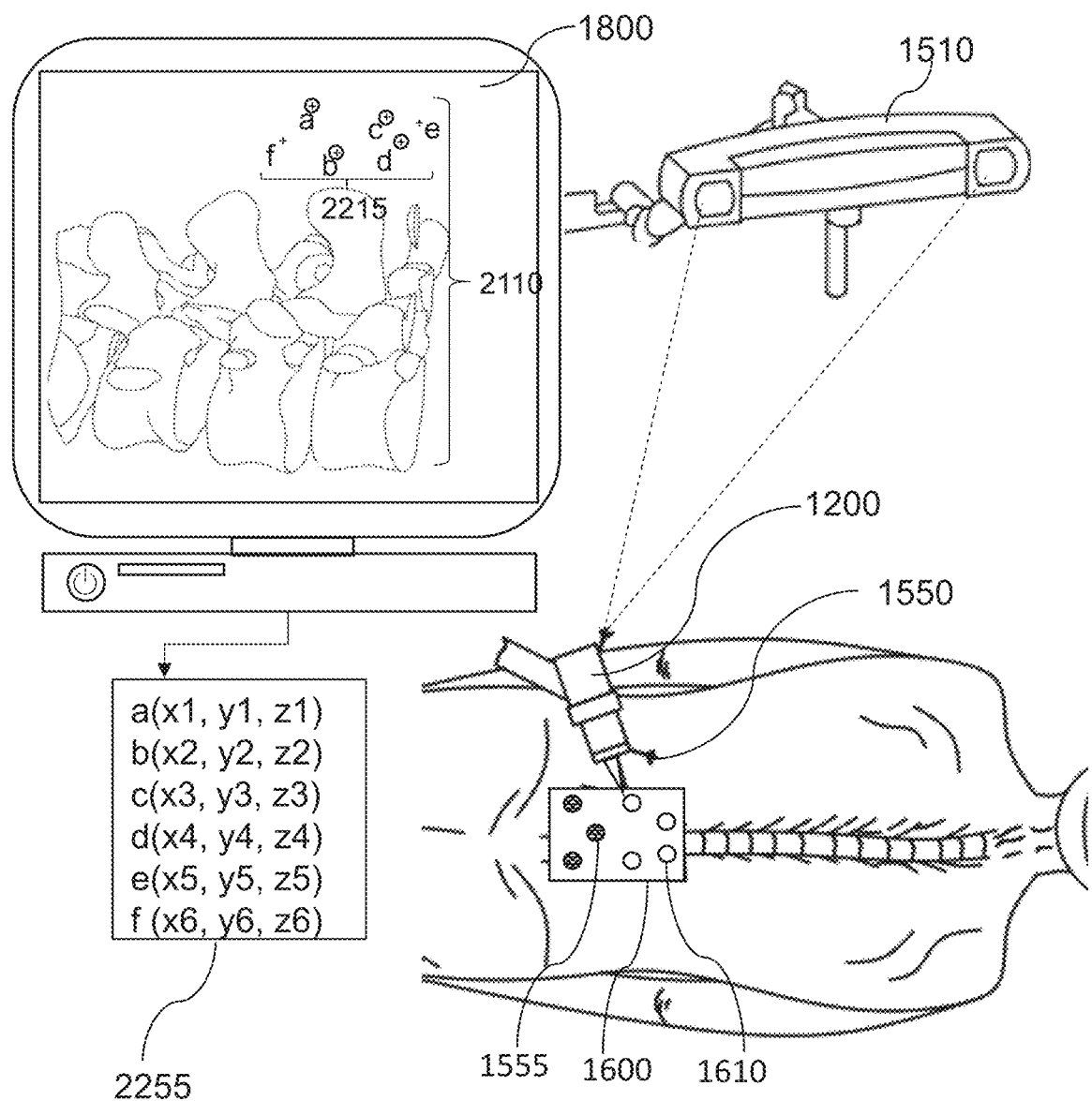
FIG. 10 is a schematic illustration of a snapshot of a registration process of the surgery assistive system in accordance with an embodiment of the present disclosure.

In Step S110, the medical imager 1910 may be a computed tomography (CT) scanner, a magnetic resonance imaging (MRI) scanner, or other commonly used medical imaging equipment that is capable of acquiring consecutive cross-sectional images of the scanned subject. In a preferred embodiment, a marker patch 1600, as illustrated in FIG. 10, is attached to the subject near the intended surgical site when the medical images are taken, to facilitate positioning of the surgical environment. Specifically, the marker patch 1600 may include at least one marker 1555 detectable by the spatial sensor 1510 of the spatial sensor system and a plurality of fiducial markers 1610 that cause markings on images taken by the medical imager 1910. The fiducial markers 1610 may be made of lead, iron, calcium, or other radiopaque metals. Therefore, as exemplified in FIG. 10, in the case where the marker patch 1600 is attached to the subject when taking the medical images, the resulting virtual anatomical model 2110 would include a plurality of radiopaque spots corresponding to the fiducial marker 1610.

In another embodiment, the markers 1555 on the marker patch 1600 may be disposed concentrically with the fiducial markers 1610 so as to avoid signal inconsistency caused by varying surface contour of the subject. Alternatively, the marker patch 1600 may be disposed with materials that are both optically readable by the spatial sensor system 1510 and radiopaque to the medical imager 1910 to ensure higher consistency between the acquired signals.

Referring again to FIG. 9. In Step S130, the user is prompted to indicate one or more locations of interest on the virtual anatomical model 2110 via the user interface 1800. The location of interest may include an intended surgical site or a specific anatomical landmark or surface feature. The user may also be allowed to label or define specific landmarks or surface features on the virtual anatomical model. In Step S141, the surgical plan generated by the method may include operative details, such as location and angle of tool entry and depth and path for the planned drilling, suggested type of tool, and suggested type of screw.

In Step 160, after the surgical plan is generated, the computer system 1700 prompts the user to begin surgery according to the surgical plan. The user may be allowed to adjust or edit the surgical plan before the surgery begins. In Step S170, the surgery assistive system 1000 assists the user during the planned surgery by adjusting the kinematic state of the manipulator 1210 according to the spatial information of the tool as detected by the spatial sensor system 1500, and informs the user via the user interface 1800. Further, in some embodiments, medical images may also be taken during the surgery to monitor the location, angle, and depth of the drilled path so as to ensure compliance with the surgical plan and to help determine the necessity to redefine a new surgical plan or to recalibrate the instrument.

After the user selects a location of his/her interest in the virtual anatomical model in Step S130, the method according to the embodiment may further include the steps of: (S151) obtaining surface information of a plurality of sampling points on the anatomical site of the subject; and (S152) assigning the surface information into the virtual anatomical model, thereby registering the virtual anatomical model into the coordinate system established by referencing the spatial information obtained by the spatial sensor system 1500.

Figure 11:
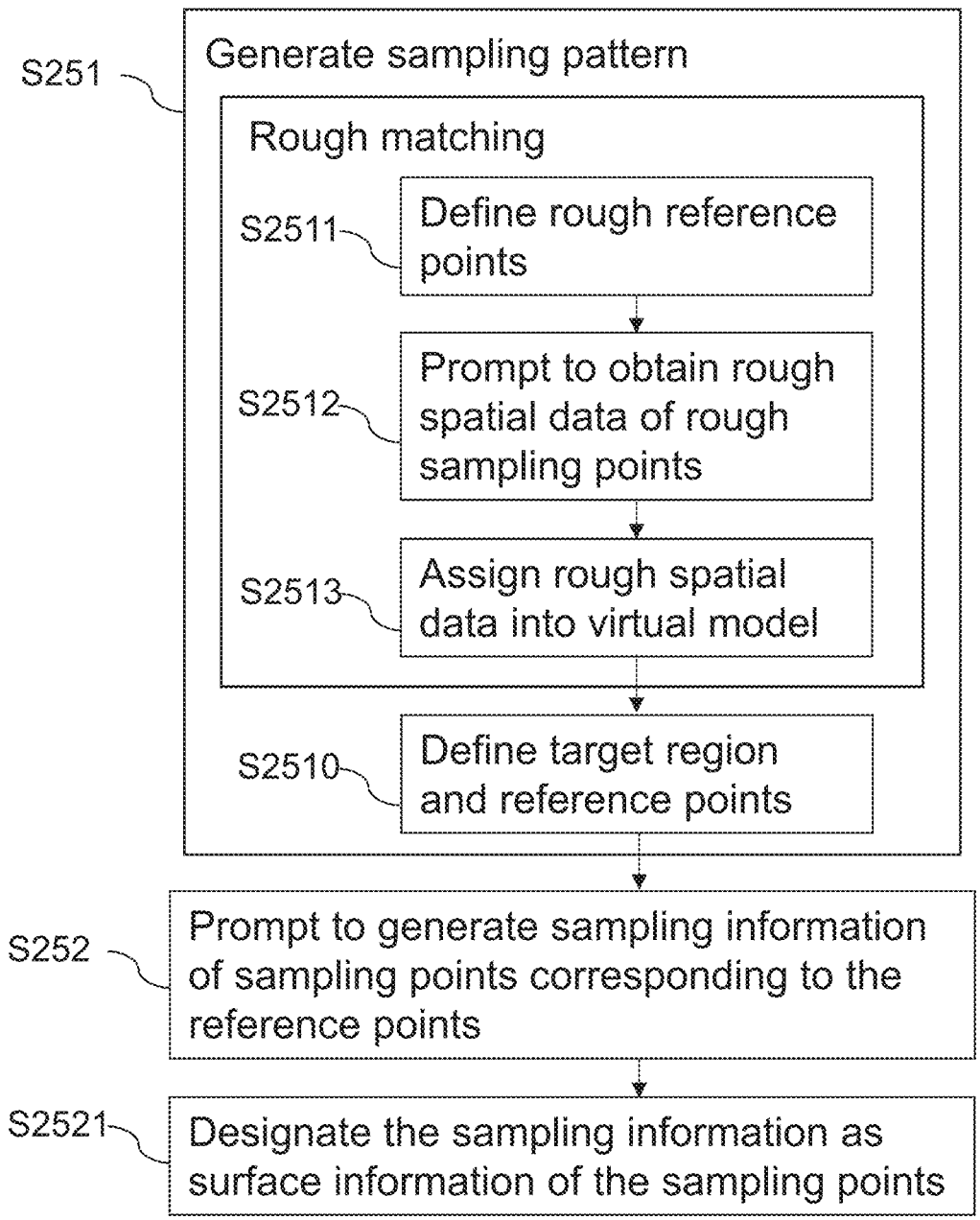
FIG. 11 is a flow diagram of the steps of obtaining surface information for registration of the surgery assistive system in accordance with an embodiment of the present disclosure.

More specifically, as shown in FIG. 11, the step S151 of obtaining surface information of the sampling points according to the embodiment includes the steps of: (S251) generating sampling pattern; (S252) prompting the user to generate sampling information of the sampling points; and (S2521) designating the sampling information as surface information of the sampling points.

Figure 12:
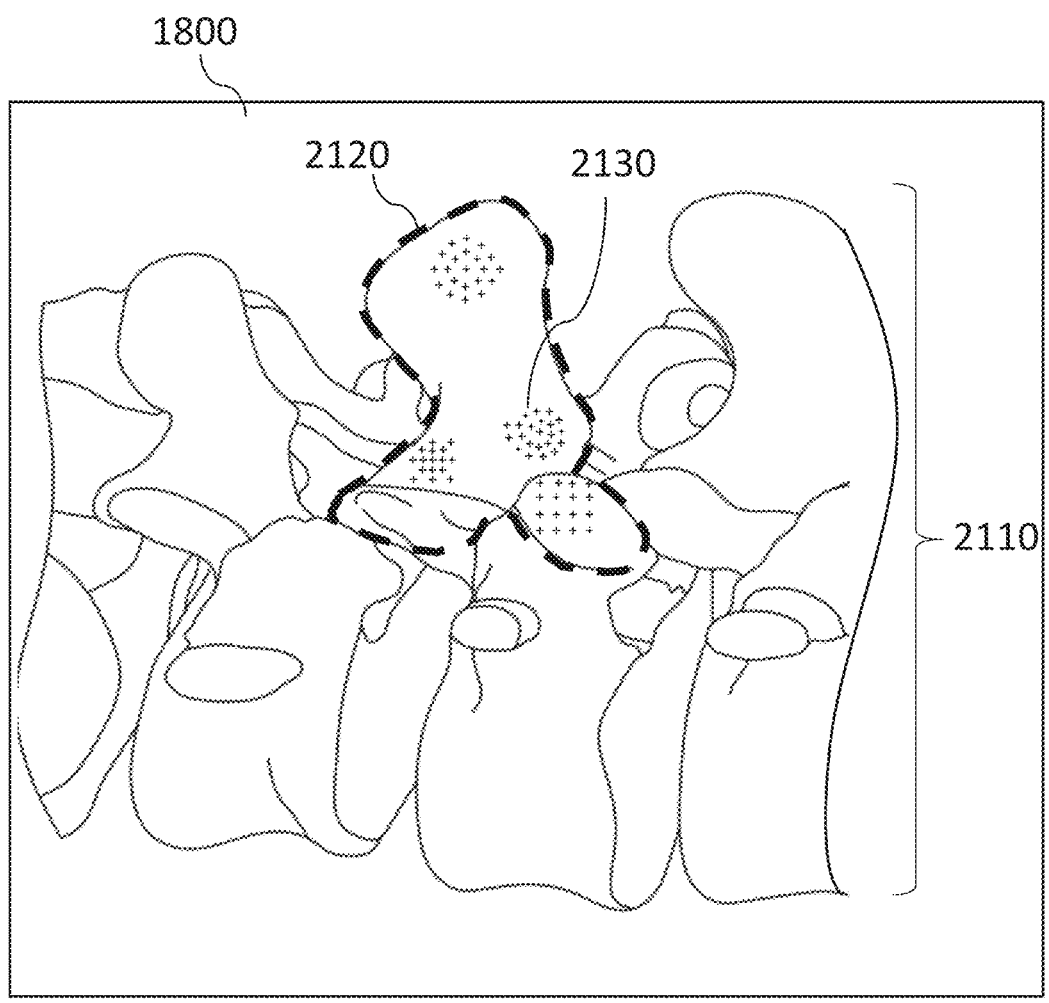
FIG. 12 is a schematic illustration of a target region and reference points generated by the surgery assistive system in accordance with an embodiment of the present disclosure.

In the embodiment, the step S251 of generating sampling pattern includes (S2510) defining a target region and a plurality of reference points on the virtual anatomical model. As illustrated in FIG. 12, after the user indicates a location of interest on the virtual anatomical model 2110 via the user interface 1800, the computer system 1700 may define a target region 2120 and a plurality of reference points 2130 in the target region. Preferably, the target region 2120 is a region having characteristic or representative surface features (e.g., facet or spinous process of a spine) or a trocar accessible region. In at least one embodiment, the references points 2130 are so distributed in target region 2120 that a plurality of surface features are covered by the reference points 2130. Preferably, the amount of the reference points 2130 may be equal to or larger than 50. The reference points 2130 may be arranged orthogonally, concentrically, spirally, or in other patterns that preferably cover a significant number of surface features. In some embodiments, targeted precision of the reference points 2130 (i.e., the distance between two adjacent reference points 2130) may be set as 3 to 4 times of the resolution of the spatial sensor 1510; for example, when the spatial sensor 1510 has a resolution of 0.25 mm, the distance between two adjacent references points may be defaulted at 1 mm. In a preferred embodiment, the targeted precision is set to about 0.3 mm. Additionally, the reference points 2130 may be prioritized according to local physiological features, such as bone density calculated from the medical images, and define a sampling route. The user may also manually define or adjust the target region 2120 and the amount and positions of the reference points via the user interface 1800.

Preferably, a matching process may be performed prior to the Step S2510 to facilitate acquisition of surface information in the subsequent steps. According to an embodiment of the present disclosure, the Step S251 of generating sampling pattern step further includes (S2511) defining a plurality of matching reference points in the target region on the virtual anatomical model; (S2512) prompting the user to generate matching spatial data by sampling a plurality of matching points on the subject corresponding to the matching reference points; and (S2513) assigning the matching spatial data into the virtual anatomical model.

In Step S2511 of the embodiment, the matching reference points may be defined by the computer system 1700 according to, for example, an imaging processing algorithm. Alternatively, the matching reference points may be defined manually by the user via the user interface 1800. As exemplified in FIG. 10, the matching reference points 2215*a-f* are preferably located close to the radiopaque spots corresponding to the fiducial marker 1610. The amount of the matching reference points may vary, and is preferably one to ten, or more preferably four to six. After the matching reference points are defined, the user is prompted to sample a plurality of matching points on or around the marker patch 1600 attached to the subject corresponding to the matching reference points 2215*a-f* using a probe installed on the instrument 1200. The matching points may be sampled one at a time by allowing the computer system to manipulate the kinematic state of the manipulator so that the tip of the probe to contact the matching points or continuously by allowing the tip of the probe to slide along a predefined matching route formed by the matching points. In the embodiment, a spatial marker frame 1550 is attached to the instrument 1200 to allow tracking of the coordinates of the probe by the spatial sensor system 1500 during sampling and thus obtaining matching spatial data 2255 corresponding to the matching reference points 2215*a-f*. Thereafter, the matching spatial data is assigned into the virtual anatomical model in Step S2512, thereby preliminarily matching the virtual anatomical model with the coordinate system recorded in the computer system 1700.

Alternatively, the matching process may be performed automatically by the surgery assistive system 1000. For example, in an embodiment of the present disclosure in which fiducial markers 1610 readable by the spatial sensor system 1510 and radiopaque to the medical imager 1910 are placed on the marker patch 1600 on the subject, the Step S251 of generating sampling pattern step further includes a step of: assigning the matching spatial data of the fiducial markers on the subject into the virtual anatomical model.

Figure 13:
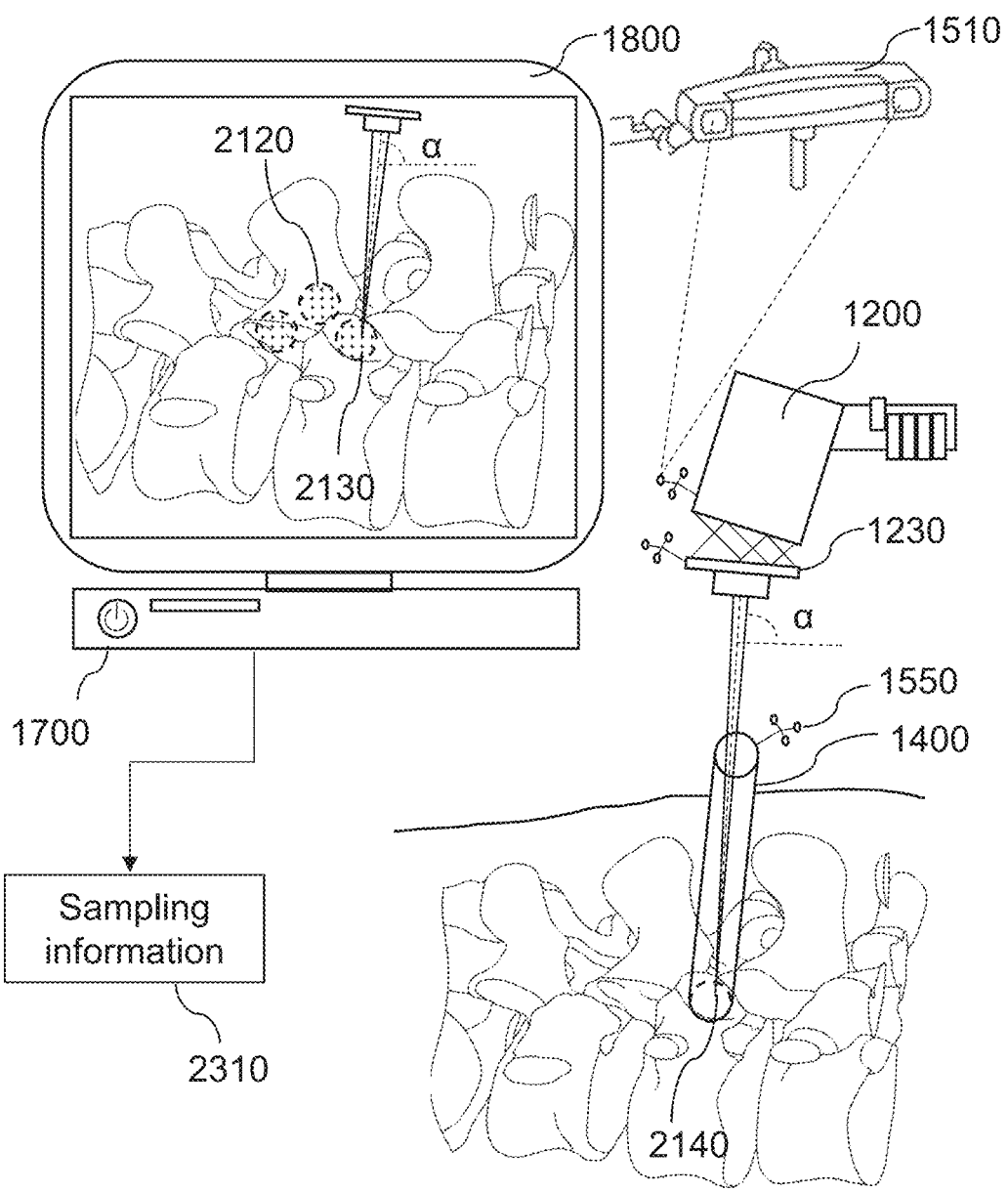
FIG. 13 is a schematic illustration of a snapshot of the registration process of the surgery assistive system in accordance with an embodiment of the present disclosure.

Referring to FIG. 13, together with FIG. 11. After the sampling pattern is generated in Step S251, the user is prompted to generate sampling information 2310 by sampling a plurality of sampling points 2140 on the subject corresponding to the reference points 2130 using a registration probe installed on the instrument 1200, as in Step S252. The sampling points may be sampled one at a time by allowing the computer system to manipulate the kinematic state of the manipulator so that the tip of the probe to contact the sampling points or continuously by allowing the tip of the probe to slide along a predefined sampling route formed by the sampling points. In the embodiment, the sampling information may include coordinates of the sampling points and angles α of contact of the probe at the sampling points as detected by the spatial sensor 1510 and parameters associated with the contacts, such as force sustained by the probe, output power of the actuator, and duration of steady contact.

In the embodiment, the force sustained by the probe including normal force (i.e., the forces parallel to the direction of the probe) and lateral force (i.e., the forces perpendicular to the direction of the probe) is detectable by the force sensor 1235 on the instrument 1200. The angle α of contact may be defined as the angle of the probe in respect to the horizontal plane. The duration of steady contact may be defined as the duration of time that the position of the spatial marker frame 1550 on the platform 1230 of the instrument 1200 remains substantially unchanged or that the acceleration, velocity, displacement, angular velocity and/or angular acceleration detected by the inertial measurement unit of the instrument 1200 remains substantially zero. Additionally, a trocar 1400 may be utilized to guide the probe during surface sampling.

After all of sampling points 2140 on the subject corresponding to the reference points 2130 are sampled in step S2521, the computer system 1700 designates or defines the sampling information as surface information of the sampling points, as in Step S2521. Referring again to FIG. 9. After the surface information is obtained in Step S151, the surface information is assigned into the virtual anatomical model generated in Step S152, thereby registering the virtual anatomical model into the coordinate system established by the spatial sensor system 1500. In the embodiment, an algorithm is employed to identify a surface region in the virtual anatomical model that fits the obtained surface information the most. The algorithm may be iterative closets point (ICP), coherent point drift (CPD) or any algorithm that minimizes the difference between two clouds of points and matches two sets of data.

In a more efficient embodiment, after a predefined amount of sampling points 2140 are sampled by the user in step S252, the computer system 1700 may assign the sampled sampling points 2140 into the virtual anatomical model while the user continues to sample the following sampling points. The results of the assignment would be displayed on the user interface 1800, so that the user can determine whether the sampled sampling points are already sufficient for registering the virtual anatomical model into the coordinate system and stop sampling the remaining sampling points accordingly.

In some embodiments of the present disclosure, the obtained surface information may be utilized to refine or improve the resolution of the virtual anatomical model generated from the medical images in Step S110, by for example updating existing surface features in the virtual anatomical model or adding new surface features to the virtual anatomical model. The surface information may also be used to update the surgical plan generated in Step S141. Alternatively, the surface information and the refined virtual anatomical model may together be utilized to update the surgical plan to ensure higher accuracy of the surgical plan.

Figure 14:
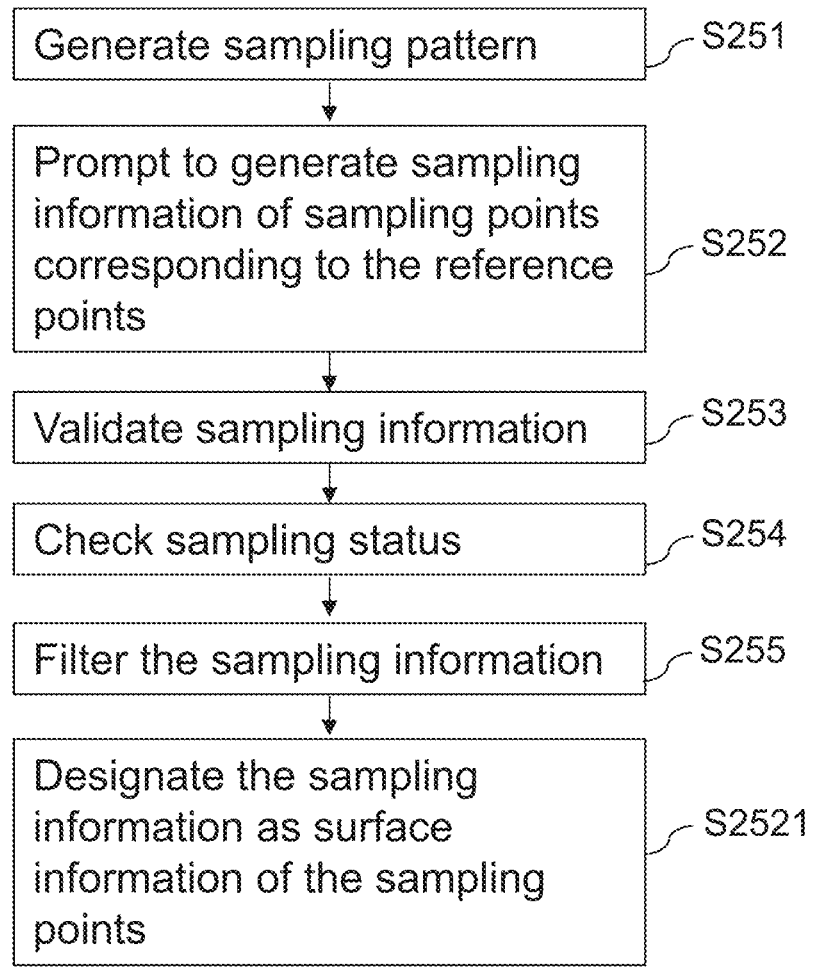
FIG. 14 is a flow diagram of the steps of obtaining surface information for registration of the surgery assistive system in accordance with an embodiment of the present disclosure.

Referring to FIG. 14. According to another embodiment of the present disclosure, the step S151 of obtaining surface information of the sampling points includes the steps of: (S251) generating sampling pattern; (S252) prompting the user to generate sampling information of the sampling points; (S253) validating a current piece of the sampling information; (S254) checking sampling status; (S255) filtering the sampling information and (S2521) designating the sampling information as surface information of the sampling points.

Figure 15:
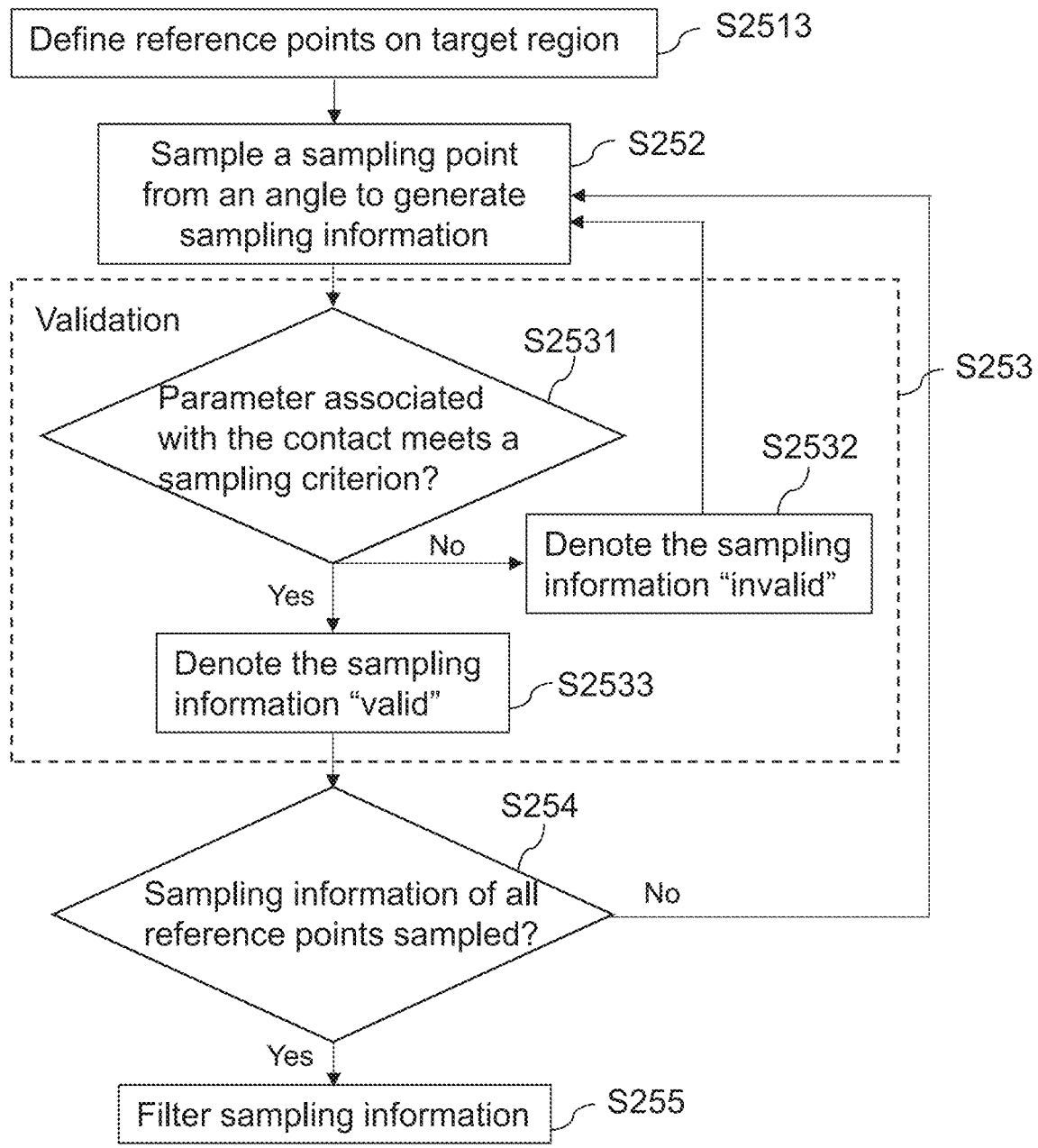
FIG. 15 is a flow diagram of the steps of validating sampling information for registration of the surgery assistive system in accordance with an embodiment of the present disclosure.

Specifically, as illustrated in FIG. 15, after the sampling information is generated in Step S252, the computer system 1700 validates the sampling information by examining the parameters according to at least one predefined sampling criterion, as in Step S253. The predefined sampling criterion may include, but is not limited to, the normal force sustained by the probe being equal to or stronger than a normal force threshold value, the lateral force sustained by the probe being equal to or weaker than a lateral force threshold value, the torque sustained by the probe being equal to or smaller than a torque threshold value, the output power of the actuator being equal to or higher than a power threshold value, and the duration of steady contact between the probe and the contacted surface being equal to or longer than a time threshold. In some embodiments, the normal force threshold value may be 5 Newton (N), the lateral force threshold value may be 0.5 N, or the torque threshold value may be 0.05 (milli-Newton×meter) mNm; the power threshold value may be 0.3 Amp; and the time threshold may be 1 second.

Referring to FIG. 15. According to an embodiment of the present disclosure, the step S253 of validating a current piece of the sampling information includes the steps of: (S2531) determining if the parameters associated with a contact included in the current piece of sampling information meets at least one of the predefined sampling criterion; (S2532) denoting the current piece of sampling information a first note if the parameters meet the sampling criterion or (S2533) denoting the current piece of sampling information a second note if the parameters do not meet the sampling criterion; and (S252) generating sampling information again when the current piece of sampling information is denoted the second note or (S254) checking sampling status when the current piece of sampling information is denoted the first note.

In the exemplary embodiment as depicted in FIG. 15, after a piece of sampling information is generated by the user contacting a sampling point 2140 on the subject corresponding to a reference point 2130 in the virtual anatomical model 2110 from an angle in Step S252, the computer system 1700 determines in Step S2531 if the parameter included in the piece of sampling information meets at least one of the sampling criterion. If the parameter does not meet the sampling criterion, the computer system 1700 would denote the sampling information "invalid" (S2532) and prompt the user via the user interface 1800 to contact the same sampling point 2140 again from a different angle (S252). In some embodiments, the computer system 1700 may skip a sampling point and prompt the user to contact the next one when sampling of that sampling point fails (e.g., the parameter does not meet the sampling criterion) consecutively for a predefined amount of times.

Alternatively, if the parameter meets the sampling criterion, the computer system 1700 would denote the piece of sampling information the first note (e.g., "valid" or "correct") (S2533) and proceed to checking the current sampling status (S254). If the sampling information of all of the sampling points corresponding to the reference points 2130 defined in Step S2513 have not been sampled, the computer system 1700 would prompt the user via the user interface 1800 to contact a next sampling point on the subject according to the predefined sampling route. The computer system 1700 repeats the validation process until all of the sampling points are correctly sampled. After all of the sampling information are sampled, the computer system 1700 proceeds to step S255 and filters the acquired sampling information by separating the invalid ones from the valid ones. Thereafter, as exemplified in FIG. 16, step S2521 is performed to designate the filtered sampling information as surface information, therefore obtaining a list of surface information of the sampling points.

In a more efficient embodiment, Step S254 may further determine whether to prompt the user to sample the next sampling point on the predefined sampling route according to key surface features associated with the sampled sampling points. The key surface features may include, but are not limited to, peak and valley on the surface as determined according to the detected direction and intensity of force sustained by the probe during sampling. If the computer system 1700 determines not to proceed as originally planned, the computer system 1700 may identify a new sampling point by, for example, deciding a direction that potentially includes one or more of the key surface features according to the parameter in the last sampling information and defining a sampling point in the direction as the next sampling point. Alternatively, the computer system 1700 may redefine the reference points or the sampling route and start sampling according the newly defined sampling route.

In sum, according to the various embodiments of the present disclosure, the surgery assistive system provides an accurate and efficient method for registration. The method defines a target region on a surface of a subject and a set of reference points distributed in the target region that covers a plurality of surface features of the surface, and validates the mechanical contacts between the probe of the surgical instrument and the surface, therefore effectively improving the accuracy and precision of computer-assisted surgeries.

Previous descriptions are only embodiments of the present disclosure and are not intended to limit the scope of the present disclosure. Many variations and modifications according to the claims and specification of the disclosure are still within the scope of the claimed disclosure. In addition, each of the embodiments and claims does not have to achieve all the advantages or characteristics disclosed. Moreover, the abstract and the title only serve to facilitate searching patent documents and are not intended in any way to limit the scope of the claimed disclosure.

What is claimed is:

1. A method for obtaining surface information, comprising:
   configuring a surgery assistive system to perform actions, comprising:
   assigning, by a computer system, matching spatial data of a plurality of fiducial markers on a subject into a virtual anatomical model, wherein the fiducial markers are readable by a spatial sensor system and radiopaque to a medical imager associated with the surgery assistive system;
   defining, by the computer system, a target region and a plurality of reference points in the target region on the virtual anatomical model of the subject, wherein the reference points are distributed in the target region where a plurality of key surface features are covered by the reference points;
   generating sampling information according to a plurality of sampling points on the subject corresponding to the reference points, wherein a tool is configured to sample the sampling points, the tool is a probe, and the computer system is further configured to manipulate a kinematic state of a manipulator to control a tip of the probe to contact the sampling points for sampling the sampling points along a predefined sampling route formed by the sampling points; wherein a first piece of the sampling information comprises a coordinate of a first sampling point of the plurality of sampling points, a first angle of a contact of the tool at the first sampling point as detected by the spatial sensor system, and first parameters associated with the contact between the tool and the first sampling point;
   determining whether at least one of the first parameters does not meet a sampling criterion which requires a specific relationship between a normal force, a lateral force or a torque detected by a force sensor, an output power of the plurality of actuators of the manipulator, or a duration of steady contact detected by an inertial measurement unit or the spatial sensor system and a threshold; wherein in response to determining that the at least one of the first parameters does not meet the sampling criterion, the tool is configured to contact the first sampling point from a second angle different from the first angle;

designating, by the computer system, the sampling information as surface information of the sampling points that meet the sampling criterion; and determining whether to sample a next sampling point on the predefined sampling route according to the key surface features associated with the sampled sampling points, wherein the key surface features include a peak and a valley on the surface as determined according to at least one of a direction and an intensity of force sustained by the tool during sampling; wherein in response to sampling the next sampling point on the predefined sampling route, the computer system identifies the next sampling point by:

deciding a direction that includes one or more of the key surface features, the key surface features being the peak and the valley on the surface as determined according to the at least one of the detected direction and intensity of force sustained by the tool during sampling, according to the parameter in a last sampling information and defining a sampling point in the direction as the next sampling point; or redefining the reference points or the sampling route and start sampling according to a newly defined sampling route;

wherein each piece of the sampling information comprises a coordinate of one of the sampling points, an angle of a contact of the tool at the one of the sampling points as detected by the spatial sensor system, and parameters associated with a contact between the tool and the one of the sampling points as detected by the force sensor; and designating, by the computer system, the sampling information as surface information of the sampling points, and assigning the surface information as surface information of the sampling points, and assigning the surface information into the virtual anatomical model, thereby registering the virtual anatomical model into a coordinate system established by the spatial sensor system;

wherein the surgery assistive system includes an instrument having the tool configured to contact or modify an anatomical surface on a body part of the subject, the force sensor for detecting a force and the torque from mechanical contacts between the tool and the anatomical surface, the manipulator, connected to the tool, having the plurality of actuators, the inertial measurement unit a platform, and a plurality of joints mounted on the platform; the spatial sensor system for detecting spatial information of the tool; and the computer system electrically connected to the instrument, the spatial sensor system, and a user interface; and performing said actions with the computer system.

2. The method according to claim 1, wherein before the defining process, the method further comprises:

preliminarily matching a virtual model with a coordinate system recorded in the computer system, the preliminary matching process comprising:

defining, by the computer system, a matching reference point in the target region on the virtual anatomical model;

generating the matching spatial data by using the tool to sample a matching point on the subject corresponding to the matching reference point; and assigning, by the computer system, the matching spatial data into the virtual anatomical model.

3. The method according to claim 1, wherein after the designating process, the method further comprises a process of: assigning the surface information into the virtual anatomical model to register the virtual anatomical model into a coordinate system.

4. The method according to claim 3, wherein after the assigning process, the method further comprises a process of: improving a resolution of the virtual anatomical model, updating existing surface features in the virtual anatomical model, or adding new surface features to the virtual anatomical model, according to the surface information.

5. The method according to claim 3, wherein after the assigning process, the method further comprises a process of: updating a surgical plan according to the surface information.

6. The method according to claim 1, further comprising:

attaching a marker patch that includes the fiducial markers readable by the spatial sensor system and radiopaque to the medical imager associated with the surgery assistive system to an intended surgical site of the subject;

acquiring, by the medical imager, a medical image with the marker patch attached on the intended surgical site, and the medical image comprises a plurality of radiopaque spots corresponding to the fiducial markers; and prompting, by the user interface, to sample the matching point on the marker patch.

7. A surgery assistive system, comprising:

an instrument comprising a tool configured to contact or modify an anatomical surface on a body part of a subject, a parallel manipulator, connected to the tool and having a plurality of actuators, a force sensor for detecting at least one of force and torque sustained by the tool, an inertial measurement unit, a platform, and a plurality of joints mounted on the platform, wherein the force sensor is connected between the tool and the parallel manipulator;

a spatial sensor system for detecting spatial information of the instrument; and a computer system electrically connected to the instrument, the spatial sensor system, and a user interface, for manipulating a kinematic state of the manipulator according to the spatial information of the tool as detected by the spatial sensor system, wherein the computer system comprises a non-transitory computer readable medium storing a program for obtaining surface information, the program is executable by at least one processor of the computer system and comprises instructions that, when executed by the processor, causes the surgery assistive system to perform actions comprising:

assigning, by the computer system, matching spatial data of a plurality of fiducial markers on the subject into a virtual anatomical model, wherein the fiducial markers are readable by the spatial sensor system and radiopaque to a medical imager associated with the surgery assistive system;

defining, by the computer system, a target region and a plurality of reference points in the target region on the virtual anatomical model of the subject, wherein the reference points are distributed in the target region where a plurality of key surface features are covered by the reference points;

generating sampling information according to a plurality of sampling points on the subject corresponding to the reference points, wherein the tool is configured to sample the sampling points, the tool is a probe, and the computer system is further configured to manipulate the kinematic state of the parallel manipulator to control a tip of the probe to contact the sampling points for sampling the sampling points along a predefined sampling route formed by the sampling points; wherein a first piece of the sampling information comprises a coordinate of a first sampling point of the plurality of sampling points, a first angle of a contact of the tool at the first sampling point as detected by the spatial sensor system, and first parameters associated with the contact between the tool and the first sampling point;

determining whether at least one of the first parameters does not meet a sampling criterion which requires a specific relationship between a normal force, a lateral force or a torque detected by the force sensor, an output power of the plurality of actuators of the parallel manipulator, or a duration of steady contact detected by the inertial measurement unit or the spatial sensor system and a threshold; wherein in response to determining that the at least one of the first parameters does not meet the sampling criterion, the tool is configured to contact the first sampling point from a second angle different from the first angle;

designating, by the computer system, the sampling information as surface information of the sampling points that meet the sampling criterion; and determining whether to prompt the user to sample a next sampling point on the predefined sampling route according to the key surface features associated with the sampled sampling points, wherein the key surface features include a peak and a valley on the surface as determined according to at least one of a direction and an intensity of force sustained by the tool during sampling; wherein in response to sampling the next sampling point on the predefined sampling route, the computer system identifies the next sampling point by:

deciding a direction that includes one or more of the key surface features, the key surface features being the peak and the valley on the surface as determined according to the at least one of the detected direction and intensity of force sustained by the tool during sampling, according to the parameter in a last sampling information and defining a sampling point in the direction as the next sampling point; or redefining the reference points or the sampling route and start sampling according to a newly defined sampling route;

wherein each piece of the sampling information comprises a coordinate of one of the sampling points, an angle of a contact of the tool at the one of the sampling points as detected by the spatial sensor system, and parameters associated with a contact between the tool and the one of the sampling points as detected by the force sensor; and designating, by the computer system, the sampling information as surface information of the sampling points, and assigning the surface information as surface information of the sampling points, and assigning the surface information into the virtual anatomical model, thereby registering the virtual anatomical model into a coordinate system established by the spatial sensor system.

8. The system according to claim 7, wherein the instrument comprises at least one handle for a user to hold onto and maneuver the instrument.

9. The system according to claim 7, wherein the surgery assistive system comprises:

the medical imager in communication with the surgery assistive system, configured to acquire medical images of the subject; and a marker patch, and the marker patch comprises the fiducial markers readable by the spatial sensor system and radiopaque to the medical imager.

10. The system according to claim 7, wherein the output power specified in the sampling criterion is required to be equal to or higher than a power threshold.

11. The system according to claim 7, wherein the duration of steady contact between the tool and one of the sampling points specified in the sampling criterion is required to be equal to or longer than a time threshold.

* * * * *